(12) United States Patent
Guillemette et al.

(10) Patent No.: US 11,850,212 B2
(45) Date of Patent: *Dec. 26, 2023

(54) MICROLAYER COEXTRUSION TO CREATE A TIME-RELEASE DRUG SUBSTANCE DELIVERY PRODUCT

(71) Applicant: Guill Tool & Engineering Co., Inc., West Warwick, RI (US)

(72) Inventors: Richard Guillemette, West Warwick, RI (US); Robert Peters, West Warwick, RI (US); Christopher Hummel, Providence, RI (US)

(73) Assignee: Guill Tool & Engineering Co., Inc., West Warwick, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/909,496

(22) Filed: Jun. 23, 2020

(65) Prior Publication Data

US 2020/0315920 A1 Oct. 8, 2020

Related U.S. Application Data

(63) Continuation of application No. 16/245,581, filed on Jan. 11, 2019, now Pat. No. 10,695,267, which is a
(Continued)

(51) Int. Cl.
| | |
|---|---|
| *A61J 3/00* | (2006.01) |
| *A61J 3/06* | (2006.01) |
| *A61J 3/07* | (2006.01) |
| *A61K 9/00* | (2006.01) |
| *A61K 9/20* | (2006.01) |
| *A61L 27/50* | (2006.01) |

(Continued)

(52) U.S. Cl.
CPC . *A61J 3/00* (2013.01); *A61J 3/06* (2013.01); *A61J 3/07* (2013.01); *A61K 9/0092* (2013.01); *A61K 9/2072* (2013.01); *A61L 27/50* (2013.01); *A61L 27/54* (2013.01); *A61L 29/14* (2013.01); *A61L 29/16* (2013.01); *A61L 31/14* (2013.01); *A61L 31/16* (2013.01); *A61L 2400/12* (2013.01); *A61L 2400/18* (2013.01)

(58) Field of Classification Search
None
See application file for complete search history.

(56) References Cited

U.S. PATENT DOCUMENTS

| | | | | |
|---|---|---|---|---|
| 4,748,189 A | * | 5/1988 | Su | G02C 7/04 514/769 |
| 4,906,246 A | * | 3/1990 | Grendahl | A61F 2/1618 623/6.28 |
| 2003/0198677 A1 | * | 10/2003 | Pryce Lewis | A61J 3/10 424/471 |

OTHER PUBLICATIONS

Collinsdictionary.com (collinsdictionary.com/dictionary/English/extrude, access date Apr. 19, 2022). (Year: 2022).*

* cited by examiner

*Primary Examiner* — Kyung S Chang
(74) *Attorney, Agent, or Firm* — Ziegler IP Law Group LLC

(57) ABSTRACT

The present disclosure relates to medical devices containing time-release drug substance, and more particularly, to medical tubing, catheters, stents, cables (including fiber optic cables), pills, capsules, sheaths, threads, clamps, sutures, and endotracheal devices. The invention also generally relates to a method for extruding multiple laminated flow streams using microlayer coextrusion to create these various time-release drug delivery products.

6 Claims, 3 Drawing Sheets

Related U.S. Application Data continuation of application No. 13/748,542, filed on Jan. 23, 2013, now Pat. No. 10,195,114, which is a continuation-in-part of application No. 13/681,413, filed on Nov. 19, 2012, now abandoned, and a continuation-in-part of application No. 13/336,825, filed on Dec. 23, 2011, now Pat. No. 9,381,712.

(60) Provisional application No. 61/561,165, filed on Nov. 17, 2011, provisional application No. 61/460,042, filed on Dec. 23, 2010.

(51) Int. Cl.
*A61L 27/54* (2006.01)
*A61L 29/14* (2006.01)
*A61L 29/16* (2006.01)
*A61L 31/16* (2006.01)
*A61L 31/14* (2006.01)

MICROLAYER COEXTRUSION TO CREATE A TIME-RELEASE DRUG SUBSTANCE DELIVERY PRODUCT

CROSS-REFERENCE TO RELATED APPLICATIONS

This application is a continuation of application Ser. No. 16/245,581 filed on Nov. 1, 2019 which is a continuation of application Ser. No. 13/748,542 filed on 23 Jan. 2013 which is a continuation-in-part of U.S. application Ser. No. 13/681,413, filed on 19 Nov. 2012, which itself claims priority to and the benefit of U.S. Provisional Application Ser. No. 61/561,165, filed on 17 Nov. 2011, and is a continuation-in-part of U.S. application Ser. No. 13/336,825, that issued as U.S. Pat. No. 9,381,712, which itself claims priority to and the benefit of U.S. Provisional Application Ser. No. 61/460,042, filed 23 Dec. 2010, the disclosures of which are incorporated herein by reference in their entireties.

FIELD

The present disclosure relates to medical devices containing time-release drug substance, and more particularly, to medical tubing, catheters, stents, cables (including fiber optic cables), pills, capsules, sheaths, implants, threads, clamps, sutures, tapes, sheets and endotracheal devices. The present disclosure also generally relates to a method for extruding multiple laminated flow streams using microlayer coextrusion to create these various time-release drug delivery products.

BACKGROUND

The use of polymers in biomedical applications has been on a rise since they were first introduced in this field. This has been possible due to the unique combination of properties exhibited by polymers such as flexibility, ease of processing and excellent biocompatibility. Biopolymers are being used in many medical devices involving life saving applications. Artificial implants, drug delivery systems, lubricious coatings for less invasive devices, biological adhesives, anti-thrombogenic coatings and soft tissue replacements are a few of the current commercial applications. Researchers around the world are trying to improve these materials to make them more versatile in their applications with an aim to eliminate the current problems associated with them.

SUMMARY

The present invention relates to an extruded medical device capable of delivering an agent in a time dependent fashion. In a microlayer extrusion process, each of a laminated flow stream(s) (containing the desired agent(s)) is subject to repeated steps in which the flows are divided and overlapped to amplify the number of laminations. The amplified laminated flows are rejoined to form a cumulated laminated output which may achieve dimensions as thin as the micro or nanometer range.

These sustained release drug emitting medical devices achieve microlayer and polymeric geometries with enhanced delivery properties.

The present invention relates to an extruded medical device comprising one or more pharmaceutical product(s) or drug substances (including mixtures thereof) layered with one or more biocompatible materials that control the time release of the delivery of the drug substance.

Medical devices include catheters, stents, threads, cables (including fiber optic cables), pills, capsules, lozenges, tablets, implants, medical tubing, sheaths, clamps, sutures, tapes, sheets and endotracheal devices.

An embodiment of the invention relates to a medical tubular device comprising: a polymeric tube containing small sized grains, nano or micro-sized features and a drug substance.

Another embodiment relates to a medical tubular device comprising multi-lumen tubes. Another more specific embodiment relates to a medical tubular device comprising two to five multi-lumen tubes in combination with one or more annular tubes.

Another embodiment relates to a medical annular device comprising: polymeric layers containing small sized grain, nano or micro-sized features and a drug substance.

Another embodiment relates to a medical tubular device with a folded annular cross-section as described herein wherein said medical device is a stent. Another embodiment of said stent contains nano or micro-sized features formed into folds or skin layers. Another embodiment of said stent containing nano or micro-sized features is formed into folds or skin layers that have separated at the fold interface.

Another embodiment relates to a medical tubular device comprising: a multi-component polymeric tube containing an embedded/extruded annular stem of a first polymer and a support surface surrounding said embedded/extruded stem containing a second polymer wherein each of said first and second polymer may contain one or more drug substances.

Another embodiment relates to a medical tubular device as described above wherein said medical tubular device is an orally administrable medicament such as a pill or capsule.

Another embodiment relates to a medical annular device as described herein wherein said medical annular device is an orally administrable medicament such as a pill or capsule.

Said medical annular device is a polymer solid comprising from two to thousands of annular layers. Any of the extruded geometries mentioned herein (such as annular, core, stem or folded) may be used to create pills or tablets. The different layers can contain different polymers each of which may or may not contain a drug, which is not necessarily the same for each layer.

Another embodiment relates to a medical device comprising a polymer solid of micro or nano sized annular rings, optionally emanating from the center of a drug substance core.

Another embodiment relates to a medical device as described above wherein said device is a pill or capsule comprising a polymer solid of annular rings.

Another embodiment relates to a medical device comprising a polymer solid of annular rings containing a drug substance emanating from a center inactive core.

Another embodiment relates to an implantable drug delivery system possessing electronic conduction properties so as to actuate a target tissue or sense a parameter associated with the target tissue. One more specific aspect of the present disclosure relates to taking a non-conductive material, such as a polymer, and creating an electrically conductive product in the nano-flow die using the polymer.

In another embodiment, making an electrically conductive product comprises filling the polymer with metal. The term "filling" is generally used to define a state where there are sufficient conductive particles within the product to establish a conductive state. As will generally be understood in the art, this can include a product layer that only partially comprises conductive elements or particles. In alternate embodiments, any suitable material that enables or provides for electrical conductivity can be used to create an electrically conductive product using the polymer, including metals.

Another embodiment relates to an implantable drug delivery systems including Reservoirs, Matrix or Osmotic pumps. For these devices, the extruded flow includes the core and stem cross sectional geometries described herein. The center area of these flows may be a drug reservoir comprising a non degradable matrix containing a drug substance or a biodegradable drug substance matrix. The outer rings may be permeable nondegradable membrane, biodegradable polymer membrane, or additional polymer layers containing drug substance or a different drug substance where dissolution of polymer controls drug release.

Another embodiment relates to an implantable drug delivery system which is an osmotic pump comprising a tubular stem cross sectional geometry flow comprising an osmotic center area of said flow and one or more outer rings comprising permeable or semipermiable nondegradable membranes.

In a reservoir drug delivery system, a concentrated drug substance core is surrounded by a permeable membrane. This membrane may be comprised of nondegradable or biodegradable polymers. The diffusivity of the membrane may be tailored using microlayer coextrusion. The annular rings created by the micro- or nano-layer die form a membrane composed of multiple polymer layers where the diffusivity is determined by the polymers used and also the layer properties created through microextrusion. In a biodegradable membrane the erosion of the membrane may also be controlled through the microlayered annular rings. In typical biodegradable systems, as the polymer degrades the surface area of the drug substance increases. This may lead to a varying drug release rate. With a microlayered time-release drug substance the thickness and concentration may be altered to achieve a more uniform and constant release. Drug substance microparticles (and/or nano particles) may also be added to individual or multiple layers. As the layers biodegrade, these drug substance particles would be released.

In another embodiment, the cumulated laminated output may comprise layers solely of drug substances. Additionally, each layer may contain a different drug substance or a different concentration or form thereof. The layers may be alternated in any suitable fashion. When the cumulated laminated output includes time-release components or layers, as each time-release layer is dissolved by the body, a layer of drug substance would be administered in a manner generally understood in the art.

Layers or layered as used herein refers to flow streams as well as the laminated output and annular geometries. Such output and geometries may have small sized grain features, generally in the range of micro and nanosized grain features. Integrated laminated streams may also have small size grain features and helical grain orientation. Layers also form as an embodiment of flow streams in the form of laminated ribbons and retain a layered structure corresponding to the number of laminations. Gradually thinner laminations may be formed within the extrusion flow, thereby obtaining smaller and smaller grain features and eventually obtaining micro or nano-sized features. The flows possess distinct boundary features.

Layers also refers to annular cross-sections of flow streams and medical devices, such as circular, elliptical, or oval shapes. Additionally, any of the extruded annular geometries mentioned herein (such as annular rings, core, stem or folded) may be used for pills or tablets. Extruded annular geometries mentioned herein (such as annular rings, core, stem or folded) may be used for implants, threads, sutures, catheters (wherein the core is hollow or a solid rod, a hollow tube, a wire, or a profile all of which may either be coextruded or extruded onto and may be comprised of any materials with or without layers. The core may also be absent.) Such geometries comprise two to thousands of such layers. The different layers can contain different polymers each of which may or may not contain a drug, which is not necessarily the same for each layer.

Some of the aspects of the disclosed embodiments are directed to forming the layers resulting in the cumulated laminated output by a microlayer coextrusion die. The microlayer coextrusion die may form the layers in annular rings that emanate from the center of the drug substance delivery device. The layers that form the drug substance containing device may be concentric. The drug substance containing polymer may be extruded in various cross-sections, such as circular, elliptical, or oval shapes. The thickness of each layer may also vary depending upon one or more factors such as the desired time release or the required dosage of the drug. The nanolayer die may be used to make the product, except that in this situation the center is not hollow.

Another embodiment of the invention relates to the time release characteristics of the produced drug delivery device may be controlled through the barrier properties of annular rings. Small micro- or nano-sized layers may induce confined polymer crystallization. These confined crystals may result in unique barrier properties. Polymer nanocomposities may also be used to control the properties of the drug substance. Particles added to the polymer may alter the diffusivity of the polymer surface or change crystal orientation. These particles may also affect barrier properties by providing a tortuous path for a permeate to travel. Permeation though the multilayer structure may be enhanced or impeded through layer size or the introduction of particles including nanoparticles.

Biocompatible materials include polymers such as polyamides, polyimides, polyureas and poly(urethane-urea)s, MPC polymer, polyesters, polyethers, etc. Polyamides such as Polyether Block Copolyamides (PEBA), medical grade polyamide 11, and MED polyamide are particularly useful polymers. Other commercially available biocompatible materials include polyvinyl pyrrolidone (PVP), Polyethylene oxide (PEO), SoluPlus™, Polyvinyl alcohol (PVA), Hydroxypropyl Cellulose (HPC), Hydroxypropylmethylcellulose Acetate Succinate (HPMCAS), Ethylene Vinyl Acetate (EVA), Methacrylates (Eudragit™), Ethyl cellulose (EC), Cellulose acetate butyrate (CAB), Cellulose Acetate Phthalate (CAP), Poly(ethylene glycol), Poly(vinyl acetate) (PVAc), Polylactide (PLA), Polyglycolide (PGA), copolymers of PLA/PGA, Polycaprolactone (PCL), Polyvinylpyrrolidone-co-vinyl acetate (Kollidon VA-64), and Polyrethanes. Nanocellulose fibers are additional biocompatible materials. Bacterial nanocellulose (BNC) is one specific nanocellulosic material embodiment. Other biocompatible materials are described in M. A. Longer and J. R. Robinson, "Sustained-release drug delivery systems," in Remington's Pharmaceutical Sciences, J. P. Remington, Ed., pp. 1676-1693, Mack Publishing, Easton, Pa, USA, 18th edition, 1990.

Another embodiment of the invention relates to the pharmaceutical product(s) or drug substances (including mixtures thereof).

In one more specific embodiment, each layer of the medical device may be comprised of one or more pharmaceutical product(s) or drug substances (including mixtures thereof) alternating with one or more materials that control the time release of the delivery of the drug substance.

The pharmaceutical products or drug substances include active pharmaceutical ingredients (API) which are dispersed and or dissolved into a polymeric matrix flow stream. The extrudate may contain amorphous solid solutions or dispersion formations. Although the aspects of the present disclosure are generally directed to drug delivery, the aspects of the disclosed embodiments are not so limited and may include any product, composition or substance, for which time release properties are desirable. These may include for example, but are not limited to, vitamins, medicaments, active and non-active ingredients.

Suitable pharmaceutical agents include antibiotics, angiogenics (such as Fibroblast growth factor (FGF), VEGF, and angiopoietins such as Ang1 and Ang2), anti-angiogentics (such as bevacizumab, thalidomide, itraconazole, carboxyamidotriazoles, angiostatin, endostatin, linomide), immunomodulators (such as immunophilins ciclosporins, rapamycins, sirolimus, zotarolimus, everolimus, glucocorticoids, cytostatics such as alkylating agents, antimetabolites), anti-inflammatories (such as salicylates, COX-2 inhibitors, propionic acid derivatives, acetic acid derivatives, enolic acid (oxicam) derivatives, fenamic acid derivatives (fenamates) and sulphonanilides), antithrombotics (such as warfarins, heparins and Factor Xa inhibitors), platelet aggregation inhibitors (such as ticlopidine or clopidogrel), antiproliferatives (such as Paclitaxel).

Other agents include neuropharmaceuticals such as antiepileptics, antipsychotics, anti-schizophrenics, and antiparkinsonian agents.

Pain medications are particularly well suited to the aforesaid methods due to the abuse remediation potential and the ability to localize the source of the active agent.

Agents useful in endocrine disorders such as hypoglycemic, insulins, glitzazones etc are also particularly amenable to the present methods. Other such endocrine related agents include parathyroid hormone, vitamin D and calcitonin.

Ophthalmic implants are also envisioned, including 2-methoxyestradiol; angiogenesis compounds such as VEGF antagonists; or corticosteroids. See for example U.S. Pat. No. 6,713,081 issued Mar. 30, 2004.

Suitable devices include a drug substance that elutes in a time dependent fashion. For example, concentrations of between 1-99 percent dry weight of the API are contemplated, more particularly 35-80 percent dry weight. Specific concentrations may be tailored to the specific pharmacologic effect desired. Such devices may also elute the drug substance for extended periods. For example some products may elute drug substance for up to 30-60 days. Other products can be designed to elute over periods of years subject only to the shelf life of the drug substance.

Another embodiment relates to pharmaceutical product(s) which are implantable devices. Implantable devices include cardiovascular related devices such as implantable pacemakers, implantable defibrillators, prosthetic heart valves, ventricular bypass (assist) devices including Left Ventricular Assist Device (LVAD), intraaortic balloon pumps, percutaneous catheters, vascular graft prostheses, catheter guidewires, vascular clamps, Pacemakers, and Implantable Cardioverter Defibrillators (ICDs).

Diabetes related devices includes continuous glucose monitoring systems including continuous subcutaneous insulin infusion (CSII) systems, insulin delivery systems such as the Insulet OmniPod® insulin management systems, Infusaid, Artificial Pancreas Device Systems (APDS), Implantable Infusion Pumps such as Medtronic's SynchroMed II and SynchroMed EL.

Anesthesiology devices include oropharyngeal airways devices (endotracheal tubes), arterial blood gas sampling devices, esophageal stethoscopes, tracheobronchial suction catheters, carbon dioxide gas analyzers, and indwelling blood oxygen partial pressure analyzers.

Auditory and balance devices include hearing aids, otoscopes, nasopharyngeal catheters, tympanostomy tubes, bronchoscopes, suction antichoke devices, cochlear Implants.

Gastrointestinal devices include enema kits, ostomy pouches, endoscopes, lithotriptors, urologic catheters, peritoneal dialysis systems, gastrointestinal tubes (such as nasogastric tubes and feeding tubes), inflatable penile implants, implanted blood access devices (vascular shunts for hemodialysis), and urogynecologic Surgical Mesh Implants.

Other devices include implantable staples, absorbable sutures, surgical drapes, surgical clips, skin adhesive, surgical mesh, facial plastic surgery prostheses (eg, nose, ear, chin), extremity splints, Gastric Banding Devices, absorbable hemostatic agents, tissue adhesives, breast implants and Hernia Surgical Mesh Implants, electroencephalograph electrodes, esthesiometers, ventricular cannulas (needles), intracranial pressure monitor devices, evoked response electrical stimulators, ventricular catheters, aneurysm clip appliers, aneurysm clips, central nervous system fluid shunts, neuromuscular stimulators, and implanted peripheral nerve stimulators, intravascular occluding catheters, cranial electrotherapy stimulators, implanted cerebellar stimulators, implanted diaphragmatic/phrenic nerve stimulators, implanted neuromuscular stimulators, electroconvulsive therapy devices, fetal scalp spiral electrodes, fetal vacuum extractors, forceps, contraceptive diaphragms, fetal scalp clip electrodes, expandable cervical dilators, and contraceptive intrauterine devices, prosthetic and surgical devices, such as many manual surgical instruments and many arthroscopic surgical instruments including arthroscopes, intramedullary fixation rods, bone cement, and certain portions of joint prostheses.

DETAILED DESCRIPTION

Figure 1:
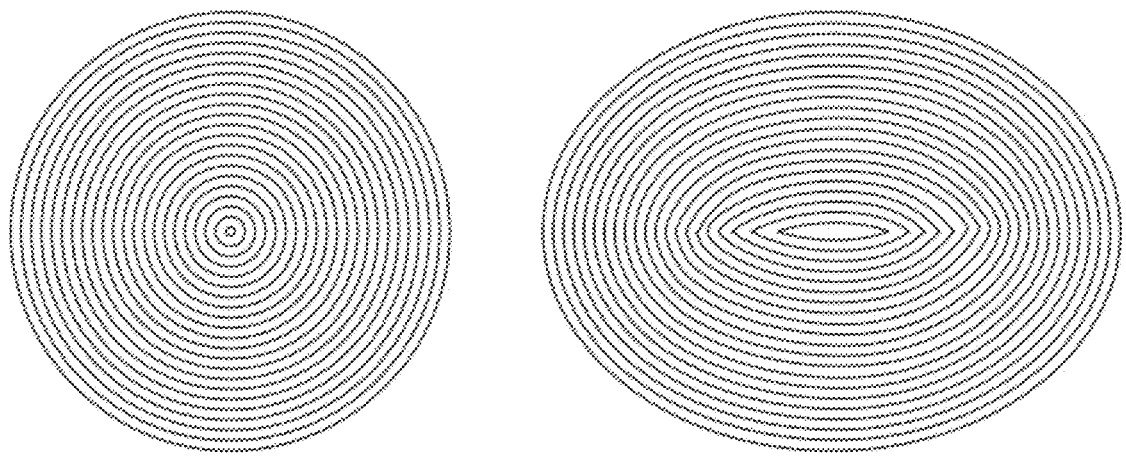
FIG. 1 illustrates a cross section of one embodiment of an annular layer drug substance made using the nanolayer die.
Figure 2:
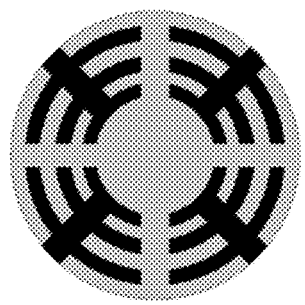
FIG. 2 illustrates one embodiment of a product created by the nano die.

General principles regarding the methods and the extrusion die may be found in United States Patent Publication No. 2012/0189789 "Method and Apparatus for Forming High Strength Products" and in U.S. Pat. No. 7,690,908 issued Apr. 6, 2010. Other methods are described in U.S. Pat. Nos. 6,669,458, 6,533,565 and 6,945,764. Each of the aforesaid publication or patent is herein incorporated by reference in its entirety.

General methods for the preparation of drug substance containing flows is known in the art. See for example Drug Dev Ind Pharm., 2005 May 31 (4-5):339-47; U.S. Pat. No. 6,488,963 to McGinity issued Dec. 3, 2002; United States Patent Publication 2011/0229526 published Sep. 22, 2011; U.S. Pat. No. 8,323,760 issued Dec. 4, 2012; and U.S. Pat. No. 8,221,778 issued Jul. 17, 2012.

General methods for further processing the cumulated laminated output into the particular sustained delivery product are well known in the art. See for example European Journal of Pharmaceutics and Biopharmaceutics, Volume 54, Issue 2, September 2002, Pages 107-117; Breitenbach J., et al., "Two Concepts, One Technology: Controlled-Release Solid Dispersions Using Melt Extrusion (Meltrex)," Drugs and the Pharmaceutical Sciences, 2008, vol. 183, pp. 179-185; U.S. Pat. No. 5,356,630 issued Oct. 18, 1994, U.S. Pat. No. 4,720,384 issued Jan. 19, 1988, U.S. Pat. No. 4,675,381 issued Jun. 23, 1987; United States Patent Publication 2007/0287800 to Acquarulo published Dec. 13, 2007; United States Patent Publication 2005/0238721 published Oct. 27, 2005 and United States Patent Publication 2004/0259969 published Dec. 23, 2004.

Implantable drug delivery systems possessing electronic conduction properties such that the implantable device may actuate a target tissue or sense a parameter associated with the target tissue are described in United States Patent Publication 2011/0230747 published Sep. 22, 2011 Rogers et al., entitled "Implantable Biomedical Devices On Bioresorbable Substrates" and U.S. Provisional Patent application 61/0658743, filed Jun. 12, 2012.

For example, a non-conductive material, such as a polymer may be transformed into an electronically conducting material by introducing an electrically conductive material into the nano-flow die processing the polymer. Making an electrically conductive product comprises filling the polymer with one or more metals or other conducting materials. The term "filling" is generally used to define a state where there are sufficient conductive particles within the product to establish a conductive state. As will generally be understood in the art, this can include a product layer that only partially comprises conductive elements or particles. Any suitable material that enables or provides for electrical conductivity can be used to create an electrically conductive product using the polymer, including metals. Circuits prepared by such methods can be controlled externally or can respond autonomously to endogenous signals within the patient such as neurotransmission including epilepsy, psychosis, or cardiac dysfunction.

Geometries

The flow streams optionally containing drug substance can be morphed into laminated ribbons retaining a layered structure corresponding to the number of laminations from gradually thinner laminations formed within the extrusion flow, thereby obtaining smaller and smaller grain features and eventually obtaining nano-sized features. These flows may possess distinct boundary features.

FIG. 1 illustrates a cross section of one embodiment of an annular layer drug substance made using the nanolayer die.

The nano die may also be used to create products which will have an increased interfacial surface area (see FIGS. 2-5). Sections of the layers mentioned above may be separated by 'stems' comprised of a single material or mixture. Each stem may be made of its own respective material or mixture allowing for the properties desired in that stem. A layer, stem or combination of the two may then be removed by some process, whether it is mechanical in nature such as peeling or chemical in nature such as dissolving. If one of the materials or mixtures used in the stem along with one or more of the materials used in the layers may all be removed, the result would be a core with stems protruding from the surface. These stems would have branches (layers) attached with a large surface area exposed to the environment. In the figure above, there are alternating layers of grey and black material separated by alternating grey and black stems. Only six layers are shown in each 'stream' for illustrative purposes but may comprise of thousands of layers. If all the black material were removed, the result would be a grey core with four stems each with six branches of material. This greatly increases the surface area exposed to the environment. By tailoring the rate at which the different materials dissolve along with the geometry, one could control the release rate of a drug substance by controlling the amount of surface area exposed to the environment. If the stems were to dissolve faster, a drug substance that broke up into sections could also be made.

Figure 3:
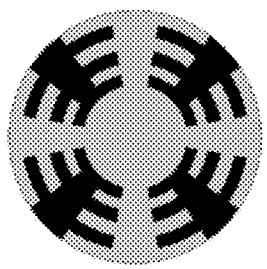
FIG. 3 illustrates another embodiment of a product created by the nano die.

In FIG. 3, the stems are tapered radially inwards. The stems may also be made to be tapered radially outwards. The stems and branches may all be made to have different thicknesses and there may be any number of each.

Figure 4:
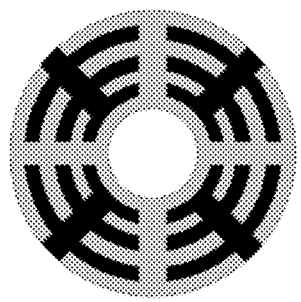
FIG. 4 illustrates another embodiment of a product created by the nano die.

In FIG. 4, above, the core is comprised of a tube made of the grey material. Examples of a core include a solid rod, a hollow tube, a wire, or a profile all of which may either be coextruded or extruded onto and may be comprised of any materials with or without layers. The core may also be absent. An outer and/or inner layer may also be added and may be composed of multiple layers and may be comprised of any suitable material or materials.

Figure 5:
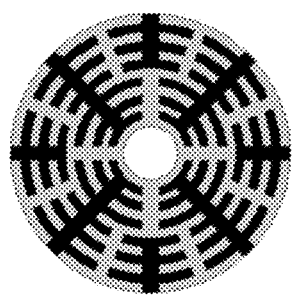
FIG. 5 illustrates a further embodiment of a product created by the nano die.

Multiple layers of streams and stems may also be used to be able to create geometries like the one pictured in FIG. 5. Theses layers may contain different numbers of layers, streams and stems in different orientations.

Folding in a Coextrusion Die

Time released drug substances may also be made through a typical coextrusion head but with layers manipulated through folding to create additional layers. Such technology is described in Patent Publication 2012/0189789 entitled "Method and Apparatus Forming High Strength Products" and U.S. Pat. No. 7,690,908 issued Apr. 6, 2010.

Figure 6:
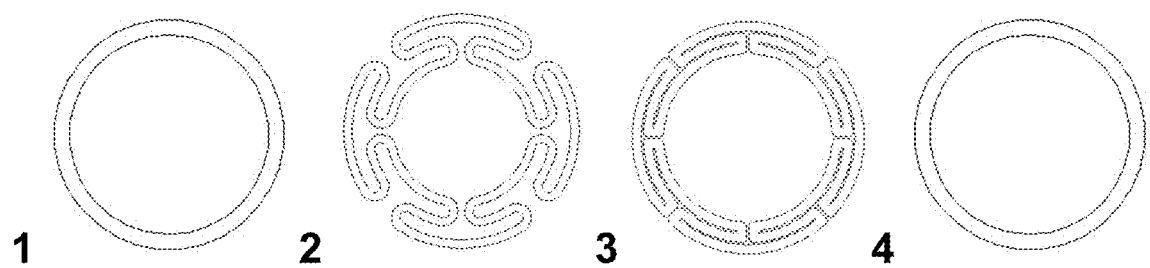
FIG. 6 illustrates a typical flow channel for a product created by the nano die.

This approach to creating multilayered products begins with a typical flow channel for a product, as is illustrated in FIG. 6 (in the example of FIG. 6 the cross-section of this flow channel is an annular ring). The flow channel is then morphed to create folds in the flow channel (steps 1 to 3). These folds are oriented and propagated in such a way so that the flow may be converged back to a flow passage with a typical cross section but now with a multiplied number of layers (step 3 to 4). One advantage of this method of layer multiplication over others is that the layers remain continuous around the product.

Figure 7:
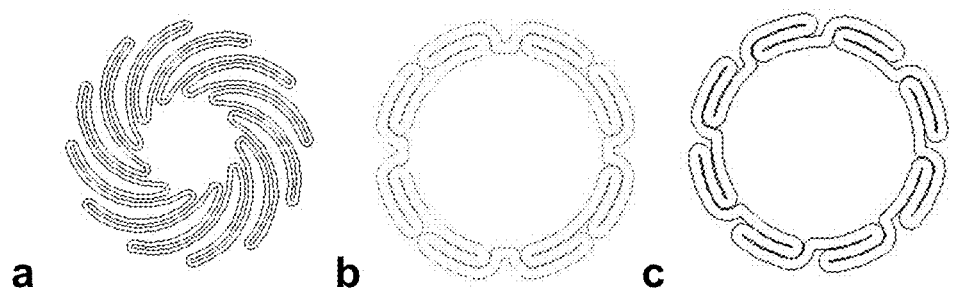
FIGS. 7a-c illustrate examples of fold structures using a layer folding technique.

Some other examples of how the folds may be oriented are illustrated in FIG. 7.

The initial flow may contain any number of suitable materials in any number of layers and the layer multiplication process may be performed multiple times. The number of folds and the relative length that they stretch may also vary.

These layer geometries formed through this method allow for a way of controlling the time release of a drug substance much like the nano die.

Stent

This aforesaid layer folding technique may also be used to create an expanding product such as a stent. A natural weakness at the interface of the folds or skin layer may be designed into a stem such that the stem can separate from the underlying support which may be dissolved either ex vivo or in vitro. The product so formed could break or separate at this interface and expand into a larger shape. This expanding product could contain a drug substance and be used in such applications as a drug substance releasing stent.

Implantable

Steams including geometric FIGS. 3 and 4 may be extruded as a hollow core or as an exudate surrounding a preformed pharmaceutical product. Such post flow extrusion work up is known to those in the art.

The invention claimed is:

1. An extrusion process for preparing a medical device comprising the steps of:
    combining at least two flow streams of laminated polymer, wherein the laminated polymer flow streams contain laminations which have micro or nanometer thickness;
    joining the at least two flow streams of laminated polymer within a die to form a continuous cumulated laminated flow within the die, extruding the continuous cumulated laminated flow to produce an extruded multilayered polymer solid of two or more annular rings, a cross-section of the extruded multilayered polymer solid having two or more annular rings with a micro or nanometer radial thickness, wherein said extruded multilayered polymer solid is further processed into a medical device which is an implantable device.

2. The process of claim 1 wherein the medical device further includes a drug substance core wherein said one or more of said annular rings emanates from the drug substance core.

3. The process of claim 2 wherein the drug substance core in the implantable device is time-released.

4. The process according to claim 1 wherein said extruded multilayered polymer solid of two or more annular rings additionally comprises at least one induced confined polymer crystallization barrier between adjacent annular rings.

5. The process according to claim 1 wherein said joined at least two flow streams of laminated polymer within a die forming the continuous cumulated laminated flow are concurrently co-extruded and additionally comprising an induced confined polymer crystallization barrier between layers of the continuous extruded multilayered polymer solid.

6. The process of claim 1 wherein the two or more of said annular rings contains a drug substance.

* * * * *